United States Patent
Bartels

(10) Patent No.: US 10,492,953 B2
(45) Date of Patent: Dec. 3, 2019

(54) EYE SURGERY PROCEDURE

(71) Applicant: Carl Zeiss Meditec AG, Jena (DE)

(72) Inventor: Andreas Bartels, Berlin (DE)

(73) Assignee: Carl Zeiss Meditec AG, Jena (DE)

( * ) Notice: Subject to any disclaimer, the term of this patent is extended or adjusted under 35 U.S.C. 154(b) by 347 days.

(21) Appl. No.: 15/278,222

(22) Filed: Sep. 28, 2016

(65) Prior Publication Data
US 2017/0087020 A1    Mar. 30, 2017

(30) Foreign Application Priority Data

Sep. 30, 2015   (DE) .................. 10 2015 218 909

(51) Int. Cl.
*A61F 9/008*        (2006.01)
*A61F 9/009*        (2006.01)

(52) U.S. Cl.
CPC ........ *A61F 9/00827* (2013.01); *A61F 9/0084* (2013.01); *A61F 9/009* (2013.01); *A61F 9/00836* (2013.01); *A61F 2009/0088* (2013.01); *A61F 2009/00872* (2013.01); *A61F 2009/00897* (2013.01)

(58) Field of Classification Search
USPC ....................................... 606/2–19
See application file for complete search history.

(56) References Cited

U.S. PATENT DOCUMENTS

| 9,084,667 | B2 | 7/2015 | Bischoff et al. | |
| 2010/0331831 | A1* | 12/2010 | Bischoff | A61F 9/008 606/5 |
| 2014/0128857 | A1* | 5/2014 | Wottke | A61F 9/00827 606/5 |

FOREIGN PATENT DOCUMENTS

| DE | 10 2007 053 281 A1 | 5/2009 |
| DE | 10 2013 218 415 A1 | 4/2014 |

OTHER PUBLICATIONS

English Language German Search Report for German Application No. 102015218909.0, dated Sep. 8, 2016.

* cited by examiner

*Primary Examiner* — Carl H Layno
*Assistant Examiner* — Dacheng Xie
(74) *Attorney, Agent, or Firm* — Patterson Thuente Pedersen, P.A.

(57) ABSTRACT

A planning apparatus for generating control data for an eye surgery treatment device which creates at least one cut surface in the cornea using a laser device. The planning apparatus includes a calculation tool for determining the at least one cut surface in the cornea. The calculation tool determines the at least one cut surface in the cornea based on data from a refractive correction and generates a set of control data that control the laser device for the at least one cut surface in the cornea. The at least one cut surface in the cornea includes an edge and optically effective areas. The calculation tool determines the at least one cut surface in the cornea such the at least one cut surface in the cornea is deeper at the edge than in the optically effective areas.

10 Claims, 5 Drawing Sheets

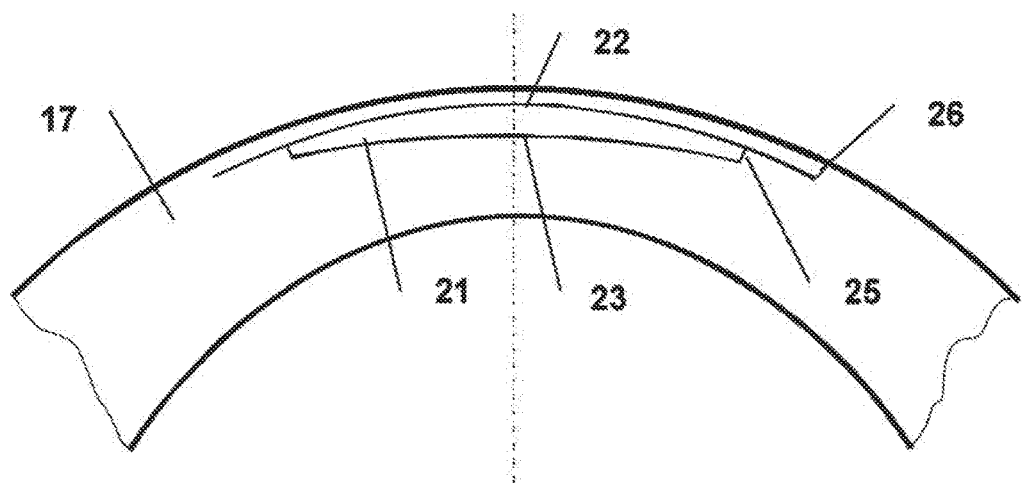
Fig. 6 (a) Prior Art
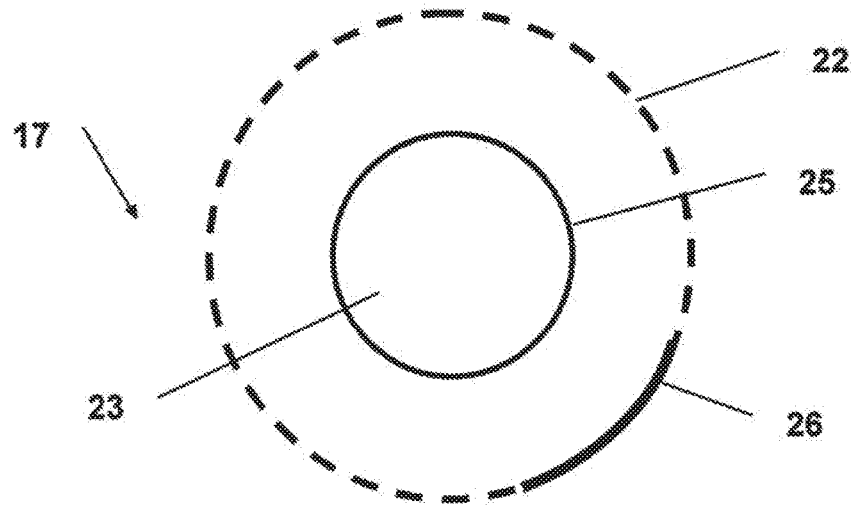
Fig. 6 (b) Prior Art

EYE SURGERY PROCEDURE

CROSS-REFERENCE TO RELATED APPLICATIONS

This application claims priority to German Application DE102015218909.0 filed Sep. 30, 2015, the entire contents of which is incorporated herein by reference.

FIELD OF THE INVENTION

The invention relates to a planning apparatus for generating control data for a treatment device which creates at least one cut surface in the cornea using a laser device. The invention also relates to a treatment device which has a planning apparatus of the aforementioned type.

The invention also relates to a procedure for generating control data for a treatment device which creates at least one cut surface in the cornea using a laser device.

The invention also relates to an eye surgery procedure whereby at least once cut surface is created in the cornea using a treatment device with a laser.

BACKGROUND

In the prior art, there are a wide variety of different treatment procedures with the aim of correcting refractive errors in the human eye which are already known. The aim of these operative methods is to alter the cornea in a targeted manner in order to influence the refraction of light in the eye. Several operative methods are used for this purpose. The most common method is the so-called laser in-situ keratomileusis, also known as LASIK. In this method, a cornea flap is detached from the cornea surface and folded to the side. This flap can be removed using a mechanical microkeratome or using a so-called femtosecond laser keratome, as sold by e.g., Intralase Corp., Irvine, USA. In a LASIK operation, after the flap has been detached and folded to the side, an excimer laser is used to remove the cornea tissue under the flap that has been exposed in this way by application of ablation. After the body under the cornea surface has been vaporized, the cornea flap is then folded back into its original place.

The use of a laser keratome to expose the flap is advantageous compared to a mechanical knife because it improves the geometric precision and reduces the frequency of clinical complications. In particular, the flap can be created with a much more consistent thickness when a laser is used. The cut edge is also formed more precisely, which lowers the risk of healing problems with this border area, which still remains after the operation. However, a disadvantage with this procedure is that two different treatment devices must be used: firstly, the laser keratome to expose the flap, and secondly, the laser to vaporize the cornea tissue.

These disadvantages are resolved by a procedure that was most recently implemented by Carl Zeiss Meditec AG and is known as FLEX (Femtosecond Lenticule EXtraction). In this lenticule extraction procedure, a short-pulse laser, for example a femtosecond laser, is used to create a geometrical cut in the eye's cornea which separates the cornea body (so-called lenticule) within the cornea. This is then removed manually by the operator after the flap covering the lenticule has been folded to the side. One advantage of this procedure is that the quality of the cut is improved even further by the use of a femtosecond laser combined with a curved contact lens.

It also means that only one treatment device is required; the excimer laser is no longer used. This method also avoids the risks and limitations associated with the excimer laser.

A development of the FLEx procedure will be referred to in this literature as the SMILE procedure, for which no flap is created, but rather only one small opening cut is made to access the lenticule under the so-called cap. The separated lenticule is extracted through this small opening incision, meaning that the biomechanical integrity of the anterior cornea is not impaired as much as with the LASIK procedure or other similar methods. This also means that on the surface, fewer nerve fibers are cut in the cornea, which will very likely have a positive effect on the recovery of the cornea surface's original sensitivity. The dry eye symptoms which often have to be treated after the LASIK procedure are therefore reduced in terms of severity and duration. Other complications after LASIK, usually associated with the flap (e.g., flap shift, wrinkles, ingrowing epithelium in the flap bed), occur more rarely without the flap.

SUMMARY

When creating a cut surface in the cornea using a laser beam, the optical beam effect is usually used to create optical penetration by application of individual optical pulses with a duration of between approximately 100 fs and 100 ns. It is also known that introducing individual pulses with an energy level that is below the threshold value for optical penetration into the tissue or material in this overlapping manner also separates the material or tissue. This concept of creating a cut in the cornea tissue allows for a wide variety of cuts. For clinical reasons, it may also be sensible for the cap cut's diameter, which defines the anterior surface of the lenticule, to be selected so that it is larger than that of the lenticule cut, which defines the diameter and the posterior surface of the lenticule (see US 2014/0128855). With the SMILE method, there are one or two opening cuts approximately orthogonal to the front surface of the eye.

However, it has become evident that in some specific cases, bubbles of plasma arising during the optical penetration also tend to spread in the cornea tissue and therefore reduce the effectiveness of the laser beam in neighboring areas, which leads to a lower incision quality and/or makes it necessary to have a higher laser power, which is not desirable. This negative effect is generally known as the Opaque Bubble Layer.

The basis of the invention is therefore the task of providing a planning apparatus for generating control data, a treatment device for corrective refractive eye surgery and a procedure for generating control data for such a treatment device, which guarantee an improved cut quality.

This task is inventively fulfilled with a planning apparatus of the type described at the beginning, which has a calculation tool to determine the cornea cut surfaces, whereby the calculation tool determines the cut surfaces in such a way that they are deeper around the edge than in the optically effective areas.

This means that the cuts begin further out and with a greater depth than would have been necessary with the previously intended incision.

The inventor discovered that these types of shaped cuts render a better cut quality and therefore greater success in terms of healing. Because the plasma bubbles usually spread in the layer of tissue in which they formed, it is therefore ensured that the actual intended cut is made above this layer, meaning that the laser beam is not hindered.

The invention also resolves the task with a treatment device that has a laser device, which cuts at least one surface in the cornea using a laser beam according to control data, and has a planning apparatus of the aforementioned type for generating control data, whereby the planning apparatus determines the cut surfaces in such a way that they are deeper around the edge than in the optically effective areas.

Finally, the invention also resolves the tasks with a procedure to generate the control data, as described at the beginning, which: Generates a set of control data for the cornea cut surfaces, transfers the control data to the treatment device and creates the cut surfaces by controlling the laser device using the set of control data, whereby during the generation of the set of control data, the cut surfaces are determined in such a way that they are deeper around the edge than in the optically effective areas.

It is clear that the aforementioned features, as well as those to be described below, can be used not only in the combinations stated, but also in other combinations or in isolation, without leaving the scope of this invention.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures.

The invention is explained in further detail below, based, for example, on the attached drawings which also disclose inventive features. These are:

FIGS. 6a and 6b are schematic sectional and frontal diagrams of SMILE lenticule geometry according to prior art;

Figure 1:
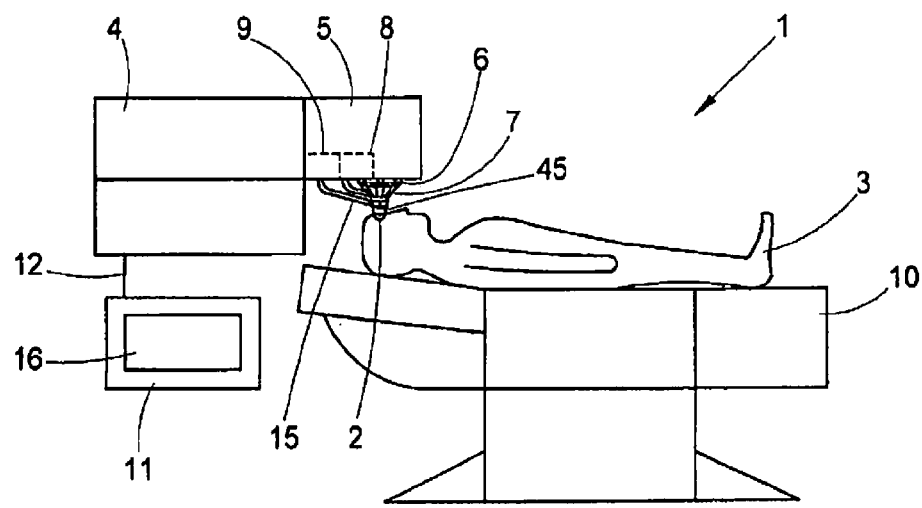
FIG. 1 is a schematic diagram of a treatment device with a planning apparatus for treatment in corrective refractive eye surgery.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION

A treatment device for eye surgery is presented in FIG. 1 and labelled with the general reference number 1. Treatment device 1 is designed to create laser cuts on the eye 2 of a patient 3. Treatment device 1 also has a laser device 4 which emits a laser beam 6 from a laser source 5, which is directed as a focused beam 7 into the eye 2 or eye's cornea. Laser beam 6 is for example a pulsed laser beam with a wavelength of between 300 nanometers and 10 micrometers. The pulse length of laser beam 6 also lies within the range of between 1 femtosecond and 100 nanoseconds, whereby it is possible for the pulse repetition rate to be between 50 and 5000 kilohertz, and for the pulse energy to be between 0.01 microjoules and 0.01 millijoules. Treatment device 1 thereby creates a cut surface in the eye's cornea 2 by deflecting the pulsed laser beam. In the laser device 4 or the laser source 5, there is also a scanner 8 and a laser beam intensity modulator 9.

The patient 3 is placed on a bed 10, which can be adjusted in three directions in order to align the eye 2 with the incoming laser beam 6. In an example design, the bed 10 can be adjusted using a motor.

The control can be done for example using a control device 11 which fundamentally controls the operation of treatment device 1 and is connected to the treatment device using suitable data connections, for example connection cables 12. Of course, this communication can take place using other methods, for example via fiber optics or radio. The control device 11 sets the appropriate settings and time control for treatment device 1, in particular for laser device 4, and in this way effectuates the relevant functions of treatment device 1.

Treatment device 1 also has a fixing apparatus 15 which holds the cornea of the eye 2 in position towards the laser device. This fixing apparatus 15 can include a known contact lens 45 which is placed onto the eye's cornea using pressure and gives the eye's cornea the desired geometric form. These types of contact lenses are known from the prior art, for example from DE 102005040338 A1. The disclosed content of this publication is fully incorporated by reference here, as far as the description of the design for any contact lens 45 that can be used in treatment device 1 is concerned. Other modified or improved contact lens designs could also be beneficial to the invention and should therefore also be included.

Treatment device 1 also has a camera which is not illustrated here, which can capture an image of the eye's cornea 17 through contact lens 45. The lighting for this camera can be either visible or infrared.

Control device 11 in treatment device 1 also has a planning apparatus 16, which will be described in more detail later.

Figure 2:
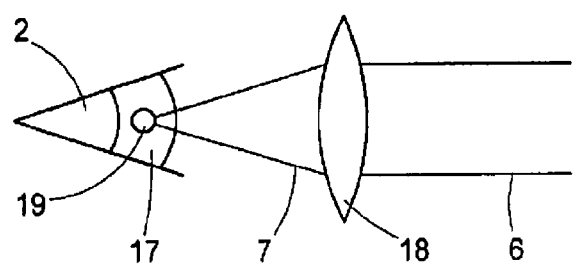
FIG. 2 is a schematic diagram of the effect of the laser beam that is used in the treatment device described in FIG. 1.

FIG. 2 schematically illustrates the way that the incoming laser beam 6 works. Laser beam 6 is focused and comes out as a focused laser beam 7 into the cornea 17 of the eye 2. There is a focusing lens which is schematically labelled as 18. This creates a focal point in the cornea 17 in that the laser beam energy density is so high that, when combined with the pulse length of pulsed laser beam 6, a non-linear effect occurs in the cornea 17. For example, every pulse of pulsed laser beam 6 in the focal point 19 creates an optical penetration in the eye's cornea 17, which in turn initiates a plasma bubble that is only indicated schematically in FIG. 2.

When a plasma bubble is formed, the separation of the tissue layer covers a larger area than the focal point 19, although the conditions for creating the optical penetration are only achieved in focal point 19. This means that for every laser pulse which creates an optical penetration, the energy density, i.e., the fluence of the laser beam, must be above a certain threshold depending on the pulse length. This relationship is known to experts from DE 69500997 T2. Alternatively, a tissue-separating effect can also be achieved using a pulsed laser beam whereby several laser beam pulses are emitted in an area where the focal points overlap. Several laser beam pulses then work together to achieve a tissue-separating effect. However, the type of tissue separation that is used in treatment device 1 is no longer relevant for the following description; the only significant factor is that a cut surface is created in the cornea 17 of the eye 2.

The invention improves pressure equalization in the plasma bubbles area while they are forming, and thus improves the cut quality with a reduction of tissue damage during the cutting procedure.

In order to carry out corrective refractive eye surgery, laser beam 6 is used to separate the cornea body from an area within the cornea 17 by separating the tissue layers in this area, isolating the cornea body and thus enabling the extraction. To isolate the cornea body which needs to be removed, for example in the case of a pulsed laser beam being applied, the position of the focal point 19 of the focused laser beam 7 is moved within the cornea 17. This is illustrated schematically in FIG. 3. The refractive properties of the cornea 17 are modified in a targeted manner by extracting the cornea body to achieve refractive correction. The body is therefore mostly lenticular in form and is referred to as the lenticule.

Figure 3:
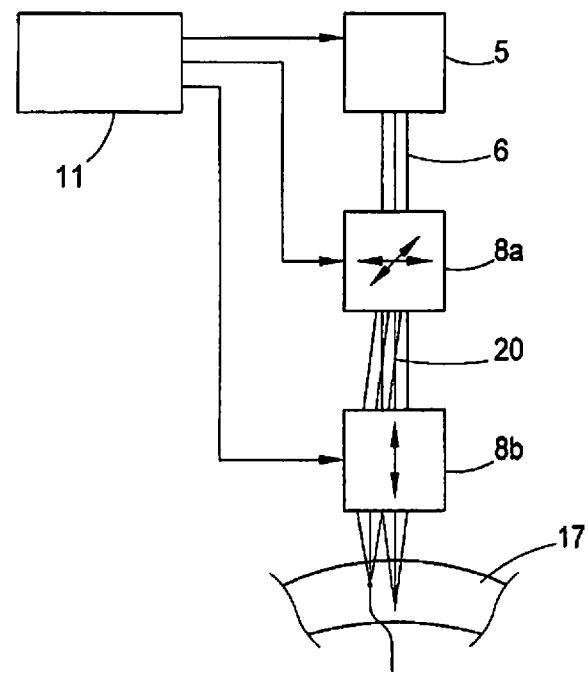
FIG. 3 is another schematic diagram of the treatment device depicted in FIG. 1 with reference to the insertion of the laser beam.

In FIG. 3, the elements of treatment device 1 are only listed as far as is necessary to understand the creation of the cut surface. As previously mentioned, laser beam 6 is focused onto a focal point 19 in the cornea 17, and the position of the focal point 19 is adjusted within the cornea so that focused energy from laser beam pulses is directed onto different spots in the cornea 17 tissue to create the cut surface. Laser beam 6 is provided by laser source 5, for example as a pulsed beam. The scanner 8 is constructed in two parts in the design shown in FIG. 3, and consists of an X-Y scanner 8a, which in one version includes of two orthogonally deflecting galvanometer mirrors. Scanner 8a deflects the laser beam 6 that comes from laser source 5 in two dimensions, so there is a deflected laser beam 20 after scanner 9. In this way, scanner 8a essentially moves the position of the focal point 19 vertically in the cornea 17 to the main incoming direction of laser beam 6. To position the depth, there is both the X-Y scanner 8a and a Z scanner 8b within scanner 8, which is designed as, by way of example, an adjustable telescope. The Z scanner 8b adjusts the Z position of the focal point 19, i.e., its position on the optical axis of the incoming beam. The Z scanner 8b can be subordinate or superordinate to the X-Y scanner 8a.

For the operating principle of treatment device 1, the allocation of individual coordinates to set the spatial position is not essential, just as scanner 8a does not need to deflect on axes that are right-angled to each other. In fact, any scanner can be used that is able to position the focal point 19 on a level which does not lie within the path of the optical beam. Furthermore, any non-Cartesian coordinates system can be used for deflecting or controlling the position of the focal point 19. Examples of this include spherical coordinates or cylindrical coordinates. The position of the focal point 19 is controlled using scanners 8a and 8b, controlled by control device 11, which sets the appropriate settings for laser source 5, modulator 9 (not shown in FIG. 3) and scanner 8. Control device 11 facilitates the proper operation of laser source 5 and the three-dimensional focal point positioning that is depicted here as an example, so that ultimately a cut surface is created which isolates a specific part of the cornea body which needs to be extracted for the purposes of refractive correction.

Control device 11 works according to the control data that is provided, which, for example, dictates the target points for the focal point positioning in laser device 4, which is depicted here purely as an example. The control data is generally collected in a control data set. This dictates the geometric requirements for the cut surface that is to be created, for example the coordinates of the target points as a model. The set of control data in this form then also includes concrete threshold values for the focal point positioning mechanism, e.g., for scanner 8.

Figure 4:
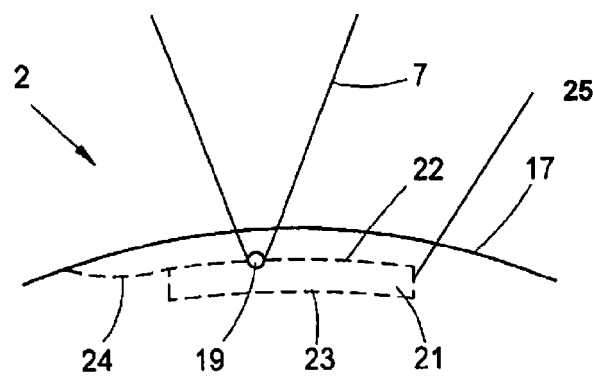
FIG. 4 is a schematic cross-sectional diagram of the eye's cornea to illustrate the extraction of a cornea body as part of corrective refractive eye surgery.

An example of creating the cut surface with treatment device 1 is shown in FIG. 4. Part of the cornea body 21 in the cornea 17 is isolated by positioning focal point 19, on which the focused beam 7 targeted. Cut surfaces also take the form of, as shown in this example, flap or cap cut surfaces 22 and posterior lenticule cut surfaces 23. These concepts are used here purely as examples and should act as references for the traditional LASIK or Flex procedures, for which treatment device 1, as already discussed, is also designed. The significant factor here is simply that cut surfaces 22 and 23, as well as the circumferential cut around the edge 25, which join the edges of cut surfaces 22 and 23, isolate the cornea body 21. Using an opening cut 24, a cornea flap bordering the anterior cornea body 21 can be folded over so that the cornea body 21 can be removed.

Alternatively, and for this invention, the SMILE procedure can essentially be used, whereby the cornea body 21 is extracted through a small opening cut, as described in DE 10 2007 019813 A1. The disclosed content of this publication is fully incorporated by reference here.

Figure 5:
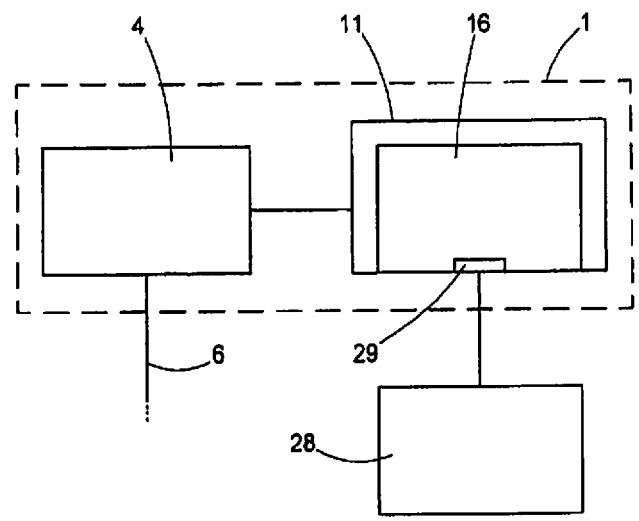
FIG. 5 is a schematic diagram illustrating the construction of the treatment device depicted in FIG. 1, with particular reference to the planning apparatus that is included as part of it.

FIG. 5 schematically depicts treatment device 1, and based on this, the significance of the planning apparatus 16 can be explained in greater detail. In this version, treatment device 1 has at least two pieces of apparatus or modules. Laser device 4, which has already been depicted, emits laser beam 6 onto the eye 2. Laser device 4 is operated, as already discussed, fully automatically by control device 11, i.e., laser device 4 begins creating and deflecting laser beam 6 when given the appropriate starting signal, creating cut surfaces which are formed in the manner described. The control signals which are necessary for operation are sent from control device 11 to laser device 5, which will have been provided with the aforementioned relevant control data. This happens by application of a planning apparatus 16, which is shown in FIG. 5 as a component of control device 11, purely as an example. Of course, the planning apparatus 16 can also be constructed separately and can communicate with control device 11 through either a wired or wireless system. The essential factor is then simply that there must be a suitable data transfer channel between the planning apparatus (16) and the control device 11.

The planning apparatus 16 generates a set of control data which is sent to control device 11 to carry out the corrective refractive eye surgery. For this, the planning apparatus uses measurement data relating to the cornea of the eye. In the version described here, this data comes from a measuring device 28 which has measured the eye 2 of the patient 3 in advance. Of course, the measuring device 28 can be constructed in any form and transfers the relevant data to the interface 29 of the planning apparatus.

The planning apparatus now assists the operator of treatment device 1 in determining the cut surface for isolating the cornea body 21. This can be up to a fully automatic determination of the cut surfaces which, for example, can cause the planning apparatus 16 to identify the cornea body 21 that needs to be removed using the measurement data, whereby the border areas of the cornea body are defined as cut surfaces and from this, the appropriate control data for control device 11 can be generated. At the other end of the automation scale, the planning apparatus 16 can have input options, in which the operator enters the geometric parameters etc. for the cut surface. Intermediate stages provide suggestions for the cut surfaces, which are automatically generated by the planning apparatus 16 and can then be modified by the operator. Essentially, all of the concepts that have already been explained in the above descriptions can be used here in the planning apparatus 16.

In order to carry out the treatment, the planning apparatus 16 generates control data to create cut surfaces which are then used in treatment device 1.

FIG. 6a shows a schematic diagram of a cornea cross-section according to prior art in the SMILE procedure to clarify the geometric proportions. The cornea 17 has an anterior cap cut 22 with an opening incision 26. The posterior lenticule cut 23 isolates the lenticule body 21, which can then be extracted through the opening incision 26.

Figure 7:
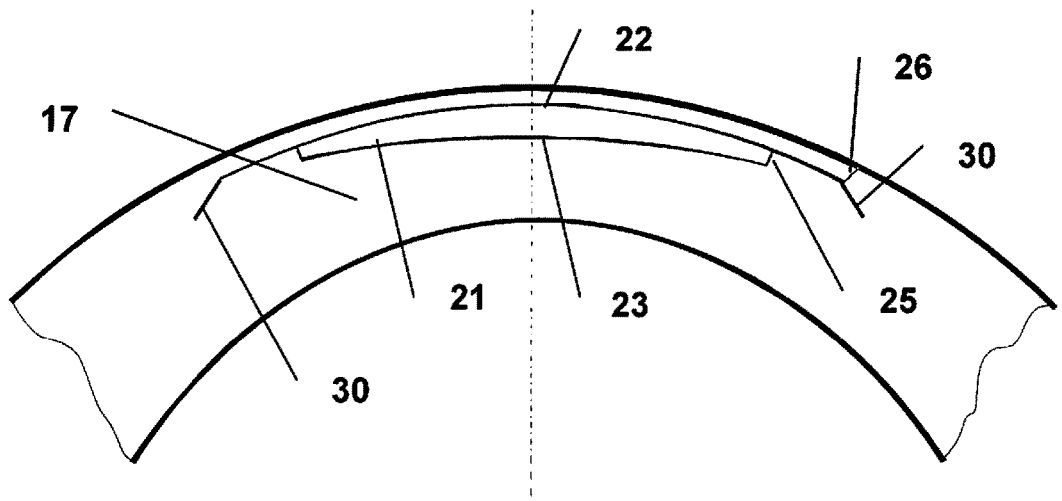
FIGS. 7a and 7b are schematic sectional and frontal diagrams of the geometry of a cut according to an example embodiment of the invention.
Figure 7:
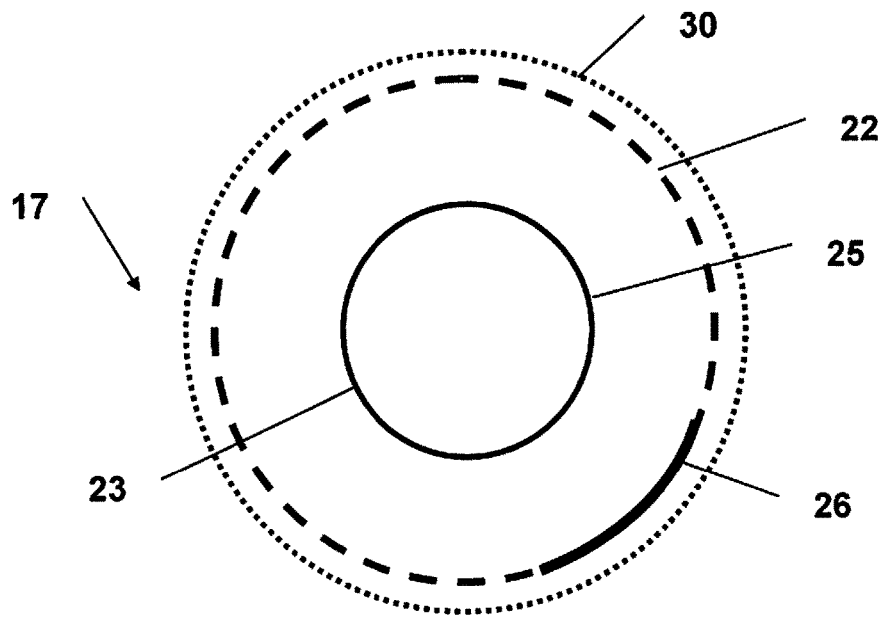

FIG. 7a shows a schematic diagram of the geometry of a cut according to an embodiment of the invention. Cap cut 22 and lenticule cut 23 match the proportions already illustrated in FIG. 6a. The cap cut 22, the diameter of which is larger than the diameter of the lenticule cut 23, is expanded over the radius which reaches the opening incision 26 and up to the edge area labelled 30. Here, the cut begins at edge area 30 at a greater depth than the depth of the cap cut (generally for example 120-180 μm). The difference between the two should for example be at least 5 μm, but can be up to 20 μm or more. Then, the depth is reduced to ultimately connect with the cap cut 22. For the purposes of simplification, edge 30 is made as a straight cut here, but it can also equally be made as a curved cut to achieve a smooth transition to the cap cut.

FIG. 7b shows an overhead view of the cornea depicted in FIG. 7a. The width of edge area 30 is approx. 0.5 μm, but it can be from 0.1 to over 1.0 mm.

In addition, it has also been noticed that treatment device 1, or rather the planning apparatus 16, of course also carries out the procedure explained previously in practice.

Another example embodiment of the planning apparatus comes in the form of a computer program, or rather a suitable data carrier with a computer program which creates the planning apparatus on a suitable computer, so measurement data is entered onto the computer via a suitable medium for data transfer and the control data is transferred from this computer to control device 11, whereby the data transfer medium in question is known to those skilled in the art.

While the invention is depicted in detail in the drawings and this description, these depictions and descriptions serve as examples only and should not be regarded as restrictive. It is clear that changes and modifications could be made by those skilled in the art within the scope of the following claims. In particular, this invention includes other embodiments with any combination of the features of the different embodiments described above and below.

Figure 8:
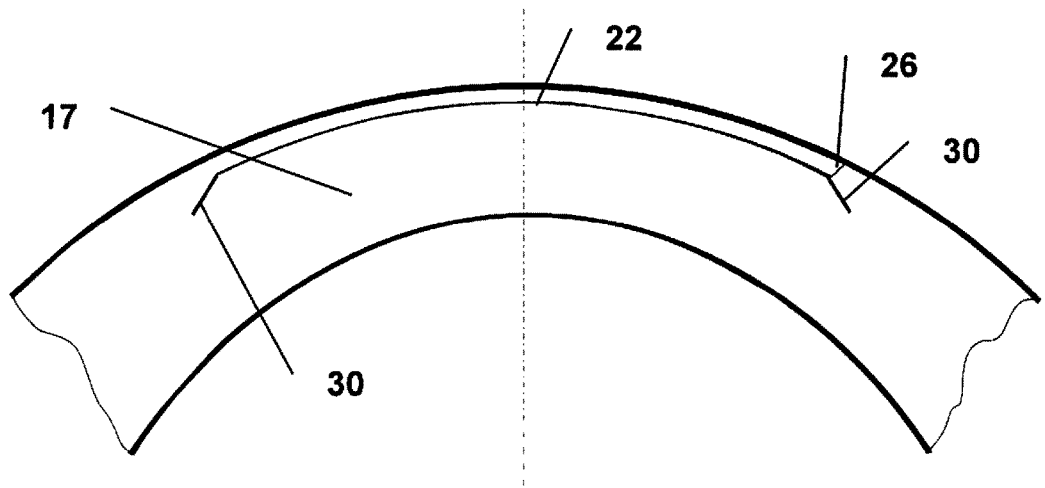
FIGS. 8a and 8b are schematic sectional and frontal diagrams of the geometry of a cut for a flap according to an example embodiment of the invention.
Figure 8:
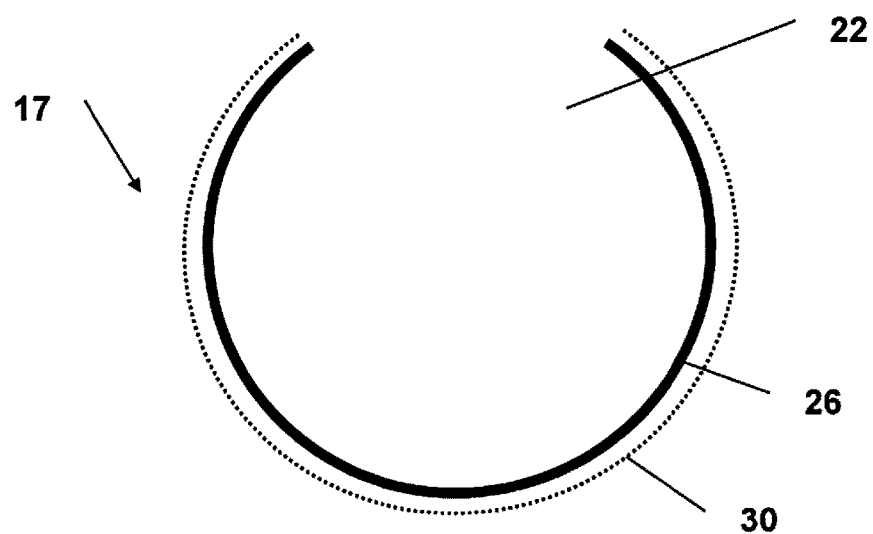

In particular, the geometry of a cut for the SMILE procedure with a cap cut and lenticule cut was described based on the invention. The invention can be used equally as well if only one flap cut is made for the LASIK or FLEx procedure. The proportions that would then result from this are described as an example in FIG. 8. Flap cut 22 has an edge area 30. This is where the edge 30 cut begins at a greater depth than the depth of the flap cut (generally for example 120-180 μm). The difference between the two should for example be at least 5 μm, but can be up to 20 μm or more. Then, the depth is reduced to ultimately connect with the flap cut 22. For the purposes of simplification, edge 30 is made as a straight cut here, but it can also equally be made as a curved cut to achieve a smooth transition to the flap cut. Here, the opening incision 26 acts as an edge cut for the flap and is located within edge area 30. However, it can also be made at the end of edge area 30 and therefore at a suitably deeper level. If necessary, this can also make the flap more stable.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method for generating control data for an eye surgery treatment device which creates at least one cut surface in the cornea using a laser device, the method comprising:
   providing cornea data based on data for a refractive correction measured prior to generating the control data;
   determining the at least one cornea cut surface, the at least one cornea cut surface having at least one optically effective area and at least one optically non-effective area; and
   generating a set of control data for the at least one cornea cut surface that control the laser device such that the at least one cornea cut surface is determined such that the at least one cut surface in the cornea is deeper at an edge thereof than in the at least one optically effective area thereof, the edge thereof being part of the at least one optically non-effective area and peripheral to the at least one optically effective area.

2. The method according to claim 1, further comprising generating the set of control data that controls the laser device to create a flap incision which does not have to use any refractive correction data to be determined.

3. The method according to claim 1, wherein the edge has a width of 0.1 to 1.0 mm and a difference in depth of 5 to 20 µm between an inner area thereof and outer areas thereof.

4. An eye surgery method in which at least two cut surfaces are created in the cornea using a treatment device with a laser device, the method comprising:
   providing cornea data based on data for a refractive correction measured prior to using the treatment device;
   determining the at least two cut surfaces to be created, including at least one lenticule cut and a cap cut based on the cornea data, the at least two cut surfaces having at least one optically effective area and at least one optically non-effective area;
   generating a set of control data for the at least two cornea cut surfaces;
   transferring the set of control data to the treatment device; and
   creating the at least two cut surfaces by controlling the laser device using the set of control data;
   wherein the at least two cornea cut surfaces are determined in such a way that at least two cornea cut surfaces are deeper at an edge thereof than in the at least one optically effective area thereof, the edge thereof being part of the at least one optically non-effective area and peripheral to the at least one optically effective area.

5. The method according to claim 4 wherein the edge has a width of 0.1 to 1.0 mm and a difference in depth of 5 to 20 µm between an inner area thereof and outer areas thereof.

6. A non-transitory computer readable data storage medium that is not a carrier wave or signal comprising program code to carry out a method for generating control data for an eye surgery treatment device which creates at least one cut surface in the cornea using a laser device, the method comprising:
   providing cornea data based on data for a refractive correction measured prior to a procedure;
   determining the at least one cornea cut surface; and
   generating a set of control data for the at least one cornea cut surface that control the laser device such that the at least one cornea cut surface is determined such the at least one cut surface in the cornea is deeper at an edge thereof than in an optically effective area thereof, the edge thereof being part of an optically non-effective area and peripheral to the optically effective area.

7. The non-transitory computer readable data storage medium according to claim 6, further comprising generating the set of control data that controls the laser device to create a flap incision which does not have to use any refractive correction data to be determined.

8. The non-transitory computer readable data storage medium according to claim 6, wherein the edge has a width of 0.1 to 1.0 mm and a difference in depth of 5 to 20 µm between an inner area thereof and outer areas thereof.

9. A non-transitory computer readable data storage medium that is not a carrier wave or signal comprising program code to carry out a method:
   the method comprising:
      providing cornea data based on data for a refractive correction measured prior to a procedure;
      determining the at least two cut surfaces, including at least one lenticule cut and a cap cut based on the cornea data;
      generating a set of control data for the at least two cornea cut surfaces;
      transferring the set of control data to the treatment device; and
      creating the at least two cut surfaces by controlling the laser device using the set of control data;
      wherein the at least two cornea cut surfaces are determined in such a way that at least two cornea cut surfaces are deeper at an edge thereof than in an optically effective area thereof, the edge thereof being part of the optically non-effective area and peripheral to the optically effective area.

10. The non-transitory computer readable data storage medium according to claim 9, further comprising creating the edge to have a width of 0.1 to 1.0 mm and a difference in depth of 5 to 20 µm between an inner area thereof and outer areas thereof.

* * * * *